(12) United States Patent
Galan et al.

(10) Patent No.: US 12,404,259 B2
(45) Date of Patent: Sep. 2, 2025

(54) INHIBITORS OF EXTRACELLULAR SIGNAL-REGULATED KINASE

(71) Applicants: GEN1E LIFESCIENCES INC., Palo Alto, CA (US); UNIVERSITY OF MARYLAND, BALTIMORE, Baltimore, MD (US)

(72) Inventors: Adam Galan, Alameda, CA (US); Ritu Lal, Palo Alto, CA (US); Chakk Ramesha, Palo Alto, CA (US); Paul S. Shapiro, Baltimore, MD (US); Alexander D. Mackerell, Jr., Baltimore, MD (US); Steven Fletcher, Baltimore, MD (US)

(73) Assignees: GEN1E LIFESCIENCES INC., Palo Alto, CA (US); UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

(21) Appl. No.: 18/920,501

(22) Filed: Oct. 18, 2024

(65) Prior Publication Data
US 2025/0129038 A1    Apr. 24, 2025

Related U.S. Application Data

(60) Provisional application No. 63/544,756, filed on Oct. 18, 2023.

(51) Int. Cl.
*C07D 333/48* (2006.01)
*A61K 31/381* (2006.01)
*A61P 35/00* (2006.01)

(52) U.S. Cl.
CPC ......... *C07D 333/48* (2013.01); *A61K 31/381* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,642,660 B2 | 2/2014 | Goldfarb | |
| 9,115,112 B2 | 8/2015 | Shapiro et al. | |
| 9,115,122 B2* | 8/2015 | Shapiro | C07D 417/06 |
| 2004/0137472 A1 | 7/2004 | Kole | |
| 2009/0163545 A1 | 6/2009 | Goldfarb | |
| 2020/0352921 A1* | 11/2020 | Liang | C07D 211/96 |

FOREIGN PATENT DOCUMENTS

| | | | |
|---|---|---|---|
| WO | 2004/089276 A2 | 10/2004 | |
| WO | 2006/018662 A2 | 2/2006 | |

OTHER PUBLICATIONS

Biava et al., Synthesis and antimycobacterial activity of new amidoderivatives of ortho-, meta- and para-toluidine, Med. Chem. Res., 8(9), 1998, pp. 523-541, 19 pages.
Guo et al., ERK/MAPK signaling pathway and tumorigenesis (Review), Experimental and Therapeutic Medicine, 19, 2020, pp. 1997-2007, 2020, doi: 10.3892/etm.2020.8454, 11 pages.
Martinez III et al., Mechanistic analysis of an extracellular signal-regulated kinase 2-interacting compound that inhibits mutant BRAF-expressing melanoma cells by inducing oxidative stress, Journal of Pharmacology and Experimental Therapeutics, 376, Jan. 2021, pp. 84-97, 31 pages.
Samadani, et al., Small-molecule inhibitors of ERK-mediated immediate early gene expression and proliferation of melanoma cells expressing mutated BRaf, Biochem. J., 467(3), May 1, 2015, pp. 425-438, doi: 10.1042/BJ20131571, 29 pages.
Song et al., Targeting RAS-RAF-MEK-ERK signaling pathway in human cancer: Current status in clinical trials, Genes & Diseases, 10, 2023, pp. 76-88, 13 pages.
Sun, et al., Discovery and antitumor evaluation of novel inhibitors of spermine oxidase, Journal of Enzyme Inhibition and Medicinal Chemistry, 34(1), 2019, pp. 1140-1151, doi: 10.1080/14756366.2019.1621863, 13 pages.
Xia et al., Synthesis and evaluation of novel inhibitors of Pim-1 and Pim-2 protein kinases, J. Med. Chem. 52(1), Jan. 8, 2009, pp. 74-86, doi: 10.1021/jm800937p., 38 pages.
Chemical properties of Naphthalene: www.chemeo.com/cid/69-516-3/Naphthalene, Chemical properties of naphthalene (CAS 91-20-3), accessed May 27, 2025, pp. 1-7.
Chemical properties of biphenyl: CAS SciFinder Registry No. 95-52-4, accessed May 27, 2025, pp. 1-42.
Chemical properties of toluene: CAS SciFinder Registry No. 108-88-3, accessed May 27, 2025, pp. 1-10.
Chemical properties of diphenyl methane: www.chemeo.com/cid/234-758-4/Diphenylomethane, Chemical properties of diphenylmethane (CAS 101-81-5), accessed May 27, 2025, pp. 1-7.
Chemical properties of diphenyl ether: CAS SciFinder Registry No. 101-84-8, accessed May 27, 2025, pp. 1-10.
Chemical properties of nitrobenzene: CAS SciFinder Registry No. 98-95-3, accessed May 27, 2025, pp. 1-26.
Biphenyl, www.pubchem.ncbi.nlm.nih.gov/compound/Biphenyl, accesed May 27, 2025, pp. 1-4.
Diphenylmethane, www.pubchem.ncbi.nlm.nih.gov/compound/diphenylmethane#section=3D-Conformer, access May 27, 2025, pp. 1-4.
Diphenylether, www.pubchem.ncbi.nlm.nih.gov/compound/7583, accessed May 27, 2025, pp. 1-4.

* cited by examiner

*Primary Examiner* — Gigi G Huang
(74) *Attorney, Agent, or Firm* — Sheppard Mullin Richter & Hampton LLP

(57) ABSTRACT

The compound 1,1-dioxido-2,3-dihydrothiophen-3-yl 4-phenoxybenzenesulfonate, pharmaceutical compositions thereof, and use of the compound and the pharmaceutical compositions for treating cancer and pulmonary diseases are disclosed.

12 Claims, No Drawings

INHIBITORS OF EXTRACELLULAR SIGNAL-REGULATED KINASE

CROSS-REFERENCE TO RELATED APPLICATIONS

This application claims the benefit under 35 U.S.C. § 119(e) of U.S. Provisional Application No. 63/544,756 filed on Oct. 18, 2023, which is incorporated by reference in its entirety.

FIELD

The present disclosure relates to inhibitors of extracellular signal-regulated kinase, pharmaceutical compositions thereof, and the use of the extracellular signal-regulated kinase inhibitors and pharmaceutical compositions thereof for treating diseases.

BACKGROUND

Allergen-induced inflammatory mediators act on immune cells and structural airways cells and activate intracellular signaling. The Activator Protein-1 (AP-1) transcription factor complex is a central regulator that responds to signaling pathways activated by cytokines, growth factors, and other inflammatory signals in airway cells to mediate airway remodeling in pulmonary diseases such as asthma. Therefore, upregulated AP-1, which contributes to multiple features of asthma pathogenesis, is an attractive anti-asthma therapeutic target. The Extracellular Signal-Regulated Protein Kinases (ERK1/2) are key regulators of AP-1 activity in airway smooth muscle (ASM), lung fibroblasts (LF), and other lung cells that contribute to the pathology of asthma. Taking advantage of ERK1/2 structural interactions with specific substrates, a unique ERK1/2 substrate docking site that mediates interactions with AP-1 complex proteins and inhibits ERK1/2-mediated AP-1 activity was identified and is described in U.S. Pat. No. 9,115,122. Targeting select kinase functions can reduce acquired drug resistance and toxicity observed with certain kinase inhibitors that target ATP binding sites and block all enzymatic activity. Considering that upregulated ERK1/2 activity contributes to the pathogenesis of pulmonary diseases such as asthma, function-selective inhibition of ERK1/2 signaling through the AP-1 can potentially mitigate ASM and LF cell hyperplasia, hypertrophy, extracellular matrix (ECM) hypersecretion, and other features of asthma.

SUMMARY

According to the present invention a compound is 1,1-dioxido-2,3-dihydrothiophen-3-yl 4-phenoxybenzenesulfonate having the structure of Formula (1):

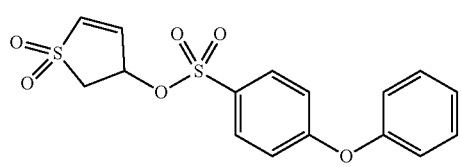

(1)

or a pharmaceutically acceptable salt thereof.

According to the present invention a compound is (S)-1,1-dioxido-2,3-dihydrothiophen-3-yl 4-phenoxybenzenesulfonate (1a):

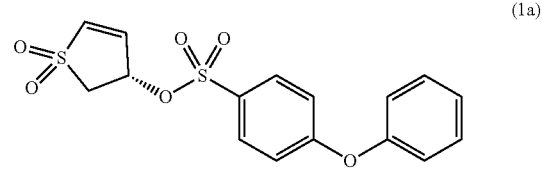 [SMILES: O=S1(=O)C=C[C@H](OS(=O)(=O)c2ccc(Oc3ccccc3)cc2)C1]

(1a)

or a pharmaceutically acceptable salt thereof.

According to the present invention a compound is (R)-1,1-dioxido-2,3-dihydrothiophen-3-yl 4-phenoxybenzenesulfonate (1b):

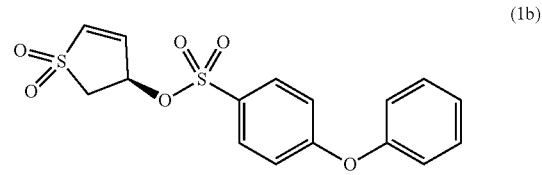 [SMILES: O=S1(=O)C=C[C@@H](OS(=O)(=O)c2ccc(Oc3ccccc3)cc2)C1]

(1b)

or a pharmaceutically acceptable salt thereof.

According to the present invention a compound is the free base.

According to the present invention a compound is the hydrochloric acid salt.

According to the present invention pharmaceutical compositions comprise a compound according to the present invention or a pharmaceutically acceptable salt thereof.

According to the present invention methods of treating a disease in a patient comprise administering to a patient in need of such treatment a therapeutically effective amount of according the present invention or a pharmaceutically acceptable salt thereof, wherein the disease is treated by inhibiting extracellular signal-regulated kinase 1 and/or extracellular signal-regulated kinase 2.

According to the present invention methods of treating a disease in a patient comprise administering to a patient in need of such treatment a therapeutically effective amount of a compound according to the present invention or a pharmaceutically acceptable salt thereof, wherein the disease is selected from cancer, an inflammatory disease, an autoimmune disease, or a pulmonary disease.

According to the present invention methods of treating a disease in a patient comprise administering to a patient in need of such treatment a therapeutically effective amount of according the present invention, wherein the disease is treated by inhibiting extracellular signal-regulated kinase 1 and/or extracellular signal-regulated kinase 2.

According to the present invention According to the present invention method of treating a disease in a patient comprise administering to a patient in need of such treatment a therapeutically effective amount of according the present invention, wherein the disease is selected from cancer, an inflammatory disease, an autoimmune disease, or a pulmonary disease.

DETAILED DESCRIPTION

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of fraction absorbed, fraction escaping gut-wall elimination, and fraction escaping hepatic elimination; and the factors that influence bioavailability can be divided into physiological, physicochemical, and biopharmaceutical factors.

"Compounds" and moieties disclosed herein include any specific compounds within the disclosed formula. Compounds may be identified either by chemical structure and/or by chemical name. Compounds are named using the ChemBioDraw Professional 17.1.0.105 (9) (CambridgeSoft, Cambridge, MA) nomenclature program. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound provided by the present disclosure or a pharmaceutically acceptable salt thereof and at least one pharmaceutically acceptable vehicle, with which the compound provided by the present disclosure, or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water or ethanol. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Solvates" refers to incorporation of solvents into to the crystal lattice of a compound described herein, in stoichiometric proportions, resulting in the formation of an adduct. Methods of making solvates include, for example, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"A compound provided by the present disclosure" refers to a compound encompassed by Formula (1) and pharmaceutically salts thereof. In certain embodiments, a compound provided by the present disclosure can further include a compound encompassed by Formula (1), pharmaceutically salts, solvates, hydrates, and/or prodrugs of any of the foregoing.

Compounds provided by the present disclosure also include crystalline and amorphous forms of the compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period relative to that achieved by administration of an immediate release formulation of the same compound by the same route of administration. In some embodiments, release of a compound occurs over period of at least about 4 hours, such as at least about 8 hours, at least about 12 hours, at least about 16 hours, at least about 20 hours, and in some embodiments, at least about 24 hours.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient, or carrier with which a compound is administered to a patient. A vehicle can be a pharmaceutically acceptable vehicle. Pharmaceutically acceptable vehicles are known in the art.

"Binding affinity" refers to the strength of the binding interaction between a single biomolecule and its ligand/binding partner. Binding affinity is expressed as the $IC_{50}$ value. Binding affinity can be determined by phage ELISA competition assays.

"Modulate" and "modulation" refer to a change in biological activity for a biological molecule such as, for example, a protein, gene, peptide, or antibody, where such change may relate to an increase in biological activity such as, for example, increased activity, agonism, activation, expression, upregulation, and/or increased expression, or decrease in biological activity such as, for example, decreased activity, antagonism, suppression, deactivation, downregulation, and/or decreased expression, for the biological molecule. For example, the compounds described herein can modulate such as inhibit ERK1/2. Compounds provided by the preset disclosure can selectively modulate, such as selectively inhibit ERK1/2 as compared to other proteins. Compounds provided by the present disclosure can selectively modulate such as selectively inhibit ERK1/2 as compared to other proteins.

"Moiety" refers to a specific segment or functional group of a molecule. Chemical moieties are often recognized chemical entities embedded in or appended to a molecule.

Reference is now made in detail to certain compounds, compositions, and methods. The disclosed compounds, compositions, and methods are not intended to be limiting of the claims. To the contrary, the claims are intended to cover all alternatives, modifications, and equivalents.

ERK, a type of serine/threonine protein kinase, is a signal transduction protein that transmits mitogen signals. ERK is generally located in the cytoplasm, and upon activation, ERK enters the nucleus and regulates transcription factor activity and gene expression. Through artificial cloning and sequencing analysis, the ERK family has been shown to consist of ERK 1, 2, 3, 5 and 6. ERK1 and ERK2 are two important members of the MAPK/ERK pathway, with molecular weights of 44 and 42 kDa, respectively.

Multiple stimulants such as growth factors, cytokines, viruses, G-protein-coupled receptor ligands and oncogenes activate the ERK pathway. Key molecules in the ERK/MAPK signaling pathway mainly include the small C proteins Ras and downstream Raf kinase, MEK1/2 and ERK1/2. Ras is the most conserved product encoded by the Ha-ras, Hi-ras and N-ras oncogenes of the ras gene family. Raf kinase is a product of the raf oncogene. MEK1 and MEK2 are rare dual-specificity kinases that can activate ERK through phosphorylation at two regulatory sites, Tyr 204/187 and Thr 202/185.

Compounds provided by the present disclosure are selective inhibitors of Extracellular Signal-Regulated Kinase ERK1/2. Pharmaceutical compositions provided by the present disclosure include compounds provided by the present disclosure. Compounds and pharmaceutical compositions provided by the present disclosure can be used to treat diseases in which the disease is treated by inhibiting ERK1/2.

Compounds provided by the present disclosure are function-selective ERK1/2 inhibitors capable of inhibiting ASM cell proliferation, AP-1 activity, and mitigating multiple features of allergic asthma in a murine model. Considering that upregulated ERK1/2 activity contributes to the pathogenesis of pulmonary diseases such as asthma, we hypothesize that function-selective inhibition of ERK1/2 signaling through the AP-1 is expected to mitigate ASM and LF cell hyperplasia, hypertrophy, extracellular matrix (ECM) hypersecretion, and other features of pulmonary diseases such as asthma.

A compound provided by the present disclosure is 1,1-dioxido-2,3-dihydrothiophen-3-yl 4-phenoxybenzenesulfonate and has the structure of Formula (1), or a pharmaceutically acceptable salt thereof:

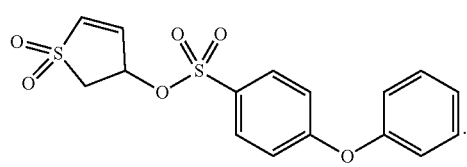

(1)

Compound (1) can be the (S)-enantiomer, (S)-1,1-dioxido-2,3-dihydrothiophen-3-yl 4-phenoxybenzenesulfonate, and have the structure of Formula (1a):

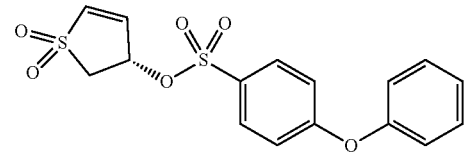 [SMILES: O=S1(=O)C=C[C@H](OS(=O)(=O)c2ccc(Oc3ccccc3)cc2)C1]

(1a)

or a pharmaceutically acceptable salt thereof.

Compound (1) can be the (R)-enantiomer, (R)-1,1-dioxido-2,3-dihydrothiophen-3-yl 4-phenoxybenzenesulfonate, and have the structure of Formula (1b):

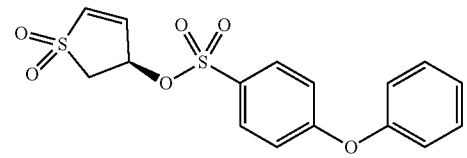 [SMILES: O=S1(=O)C=C[C@@H](OS(=O)(=O)c2ccc(Oc3ccccc3)cc2)C1]

(1b)

or a pharmaceutically acceptable salt thereof.

Reference to the compound of Formula (1) includes reference to the compounds of Formula (1), Formula (1a), and Formula (1b).

A compound of Formula (1) can be a solvate, a pharmaceutically acceptable salt, or a combination thereof.

In a compound of Formula (1), a pharmaceutically acceptable salt can be the hydrochloride salt.

A compound of Formula (1) can be a pharmaceutically acceptable salt of a compound of Formula (6), a hydrate thereof, or a solvate of any of the foregoing.

Compounds of Formula (1) can be synthesized adapting methods as described, for example, in Martinez et al., *Journal of Pharmacology and Experimental Therapeutics*, January 2021, Vol. 376, pages 84-97; and in U.S. Pat. No. 9,115,122.

A compound of Formula (1) can be an ERK1/2 inhibitor such as a selective ERK1/2 inhibitor and/or a modulator of ERK1/2 protein activity.

A compound of Formula (1) can be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. A pharmaceutical composition provided by the present disclosure can be injectable intravenous formulation. A pharmaceutical composition provided by the present disclosure can be an oral formulation. An oral formulation can be an oral dosage form. A pharmaceutical composition can be formulated for intravenous administration or for subcutaneous administration.

A pharmaceutical composition provided by the present disclosure can comprise a therapeutically effective amount of a compound of Formula (1) together with a suitable amount of one or more pharmaceutically acceptable vehicles so as to provide a composition for proper administration to a patient. Suitable pharmaceutical vehicles and methods of preparing pharmaceutical compositions are described in the art.

Assessing single patient response to therapy and qualifying a patient for optimal therapy are among the greatest challenges of modern healthcare and motivate trends in personalized medicine. A compound of Formula (1) can have target selectivity, for example, for certain cancers and immune cells. A compound of Formula (1) radiolabeled for positron emission tomography (PET) or Single Photon Emission Computed Tomography (SPECT) can be used to predict the targeting of the treatment based on a single-study, case-by-case patient analysis thus excluding patients that are expected not to benefit from treatment. PET/SPECT scans using a compound of Formula (1), once correlated to the concentration can provide a three-dimensional distribution map, which can then be used for macroscopic dose calculations.

A compound of Formula (1) and/or pharmaceutical composition thereof can generally be used in an amount effective to achieve an intended purpose. For use to treat a disease such as cancer, an autoimmune disease or an inflammatory disease, a compound of Formula (1) and/or pharmaceutical composition thereof, may be administered or applied in a therapeutically effective amount.

The amount of a compound of Formula (1) and/or pharmaceutical composition of any of the foregoing that will be effective in the treatment of a particular disorder or condition will depend in part on the nature of the disorder or condition, and can be determined by standard clinical techniques known in the art. In addition, in vitro or in vivo assays may optionally be employed to help identify optimal dosage ranges. The amount of a compound of Formula (1), and/or pharmaceutical composition of any of the foregoing administered will depend on, among other factors, the patient being treated, the weight of the patient, the severity of the affliction, the manner of administration and the judgment of the prescribing physician.

A compound of Formula (1) can be assayed in vitro and in vivo, for the desired therapeutic activity, prior to use in humans. For example, in vitro assays may be used to determine whether administration of a specific compound or a combination of compounds is preferred. The compounds can also be demonstrated to be effective and safe using animal model systems.

In certain embodiments, a therapeutically effective dose of a compound of Formula (1) and/or pharmaceutical composition of any of the foregoing will provide therapeutic benefit without causing substantial toxicity. Toxicity of a compound of Formula (1) and/or pharmaceutical compositions of any of the foregoing may be determined using standard pharmaceutical procedures and may be readily ascertained by the skilled artisan. The dose ratio between toxic and therapeutic effect is the therapeutic index. A compound of Formula (1) and/or pharmaceutical composition of any of the foregoing exhibits a particularly high therapeutic index in treating disease and disorders. A dose of a compound of Formula (1) compound, and/or pharmaceutical composition of any of the foregoing will be within a range of circulating concentrations that include an effective dose with minimal toxicity.

Compounds and pharmaceutical compositions provided by the present disclosure can be included in a kit that can be used to administer the compound to a patient for therapeutic purposes. A kit can include a pharmaceutical composition comprising a compound provided by the present disclosure suitable for administration to a patient and instructions for administering the pharmaceutical composition to the patient. The kit can be suitable for treating cancer, for treating an autoimmune disease, or for treating an inflammatory disease. A kit for use in treating cancer, for treating an autoimmune disease, or for treating an inflammatory disease can comprise a compound or a pharmaceutical composition provided by the present disclosure, and instructions for administering the compound to a patient.

Compounds and pharmaceutical compositions provided by the present disclosure can be included in a container, pack, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compounds and pharmaceutical compositions provided by the present disclosure can be used to treat a disease in a patient.

Compounds and pharmaceutical compositions provided by the present disclosure can be used to treat a disease in which the etiology of the disease is associated with up-regulation and/or down-regulation of ERK1/2.

Methods provided by the present disclosure include treating a disease in a patient comprising administering to a patient in need of such treatment a therapeutically effective amount of a compound or composition provided by the present disclosure, wherein the disease is treated by inhibiting ERK1/2.

Asthma is an obstructive pulmonary disease that impacts the quality of life for over 230 million people worldwide. Airway inflammation is fundamental to asthma pathology and chronic inflammation leads to airway remodeling (AR) characterized by structural and secretory changes in multiple lung cell types. There are currently no effective pharmacological anti-asthma therapies that prevent or reverse AR although AR is directly correlated with reduced pulmonary function and morbidity in asthma. Significant strides have been made in developing immunologics for asthma treatment, however, the heterogeneity of inflammation (Th2 high vs. low) among asthmatics significantly limits the use of biologicals in asthma. Thus, identification of key downstream effectors including transcriptional regulators and rational design of drugs targeting these effectors will help facilitate new treatment for asthma. The Activator Protein-1 (AP-1) transcription factor complex is one such central regulator at which mediators of asthma pathology converge. Also, AP-1 cooperates with other transcription factors, including NF-κB and STAT proteins to mediate inflammatory responses in asthma.

The mitogen-activated protein kinases (MAPK), which include the extracellular signal-regulated kinases (ERK1/2), c-Jun N-terminal kinases (JNK1/2), and the p38 MAPK family, are major regulators of AP-1 proteins. It has been well documented that ERK1/2 signaling is perturbed in asthma and is a predominant regulator of airway smooth muscle (ASM) cell proliferation, a key component of AR. As such, inhibiting ERK1/2 is an attractive therapeutic approach to mitigate AR. However, ERK1/2 regulate hundreds of substrates, some of which are essential for normal cell function and may have pro- or anti-asthmatic functions. Thus, ATP-competitive inhibitors developed to inhibit ERK1/2 block all kinase activity and have limited efficacy due to off-target effects, toxicity, and the invariable induction of drug resistance.

Compounds provided by the present disclosure target ERK1/2 interactions with substrates in the AP-1 complex and inhibits AP-1 activity in multiple cell lines, including ASM cells. Structural studies demonstrate the requirement for the formation of a covalent adduct with a cysteine residue (C252) that is part of a unique ERK1/2 docking site that mediates interactions with AP-1 complex proteins. Importantly, C252 is unique to ERK1/2 and analogous cysteines are not found on other major MAP kinases such as ERK5, p38α/β, or JNK1/2. Compounds provided by the present disclosure inhibit PDGF-induced proliferation and secretory function of ASM cells and mitigates AR and other pathological features including airway inflammation and hyperresponsiveness in a mouse model of asthma.

ERK1/2 kinases are associated with the pathogenesis of many human diseases, including, for example, cancer, rheumatoid arthritis, cardiovascular disease, multiple sclerosis, inflammatory bowel disease, chronic obstructive pulmonary disease (COPD), asthma, acute respiratory distress syndrome (ARDS), and acute lung injury (ALI). Among the many important biological processes regulated by ERK1/2, regulation of endothelial and epithelial barrier function, leukocyte trafficking, and cytokine expression are central to the pathogenesis of acute and chronic inflammatory disorders.

Methods provided by the present disclosure include methods of treating a disease in a patient comprising administering to a patient in need thereof a therapeutically effective amount of a compound or pharmaceutical composition provided by the present disclosure, wherein the disease is selected from acute coronary syndrome, acute lung injury, acute respiratory distress syndrome (ARDS), Alzheimer's disease, asthma, a cardiovascular disease, chronic obstructive pulmonary disease (COPD), asthma, inflammatory bowel disease, major depressive disorder, multiple sclerosis, neuropathic pain, and rheumatoid arthritis.

Compounds and pharmaceutical compositions provided by the present disclosure may be used for treating cancer in a patient. The cancer can be, for example, a solid tumor or a metastasis.

Methods provided by the present disclosure include methods of treating cancer in a patient comprising administering to a patient in need thereof a therapeutically effective amount of a compound or pharmaceutical composition provided by the present disclosure.

Examples of suitable cancers include acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, and Hodgkin's disease.

Examples of suitable cancers include pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma. A cancer can be acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilms tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom macroglobulinemia.

Compounds and pharmaceutical compositions provided by the present disclosure can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, small intestine cancer, soft tissue sarcoma, squamous cell carcinoma (nonmelanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenström macroglobulinemia, Wilms tumor, and systemic and central metastases of any of the foregoing.

Methods provided by the present disclosure include methods of treating cancer, where the cancer is selected from breast cancer and melanoma.

Methods provided by the present disclosure include methods of treating an inflammatory disease in a patient comprising administering to a patient in need thereof a therapeutically effective amount of a compound or pharmaceutical composition provided by the present disclosure.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Methods provided by the present disclosure include methods of treating an inflammatory disease in a patient, where the inflammatory disease is selected from, for example, acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes including Type 1 diabetes and Type 2 diabetes, and rheumatoid arthritis.

Methods provided by the present disclosure include methods of treating an autoimmune disease in a patient comprising administering to a patient in need thereof a therapeutically effective amount of a compound or pharmaceutical composition provided by the present disclosure.

A compound or a pharmaceutical composition provided by the present disclosure can be useful in treating autoimmune diseases. Autoimmune diseases can be defined as human diseases in which the immune system attacks its own proteins, cells, and/or tissues. A comprehensive listing and review of autoimmune diseases can be found, for example, in *The Autoimmune Diseases*, Rose and Mackay, 2014, Academic Press.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Bechet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan' syndrome, cold agglutinin disease, congenital heart block, Coxcackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Gullain-Barre syndrome, Hashimoto's thyroiditis, hemolytic anemia, Henoch-Schoenlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonnage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vaculitis, vitiligo, and Wegener's granulomatosis.

A compound or a pharmaceutical composition provided by the present disclosure can be used to treat autoimmune disorders such as, for example, lupus, graft-versus-host disease, hepatitis C-induced vasculitis, Type I diabetes, multiple sclerosis, spontaneous loss of pregnancy, an atopic disease, and an inflammatory bowel disease.

A compound or a pharmaceutical composition provided by the present disclosure can be administered with one or more additional therapeutic agents for treating an autoimmune disease. A compound of Formula (1) or a pharmaceutical composition thereof may be administered in conjunction with one or more immunosuppressants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

Methods provided by the present disclosure include methods of treating a disease in a patient comprising administering to a patient in need thereof a therapeutically effective amount of a compound or pharmaceutical composition provided by the present disclosure, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

A compound or a pharmaceutical composition provided by the present disclosure can be administered with one or more additional therapeutic agents for treating an age-related disease such as hearing loss, muscle regeneration, and Werner's syndrome.

Methods provided by the present disclosure include methods of treating a disease in a patient comprising administering to a patient in need thereof a therapeutically effective amount of a compound or pharmaceutical composition provided by the present disclosure, wherein the disease is an age-related disease such as, for example, hearing loss, muscle degeneration, Werner's syndrome, cellular aging, or Alzheimer's disease.

Methods provided by the present disclosure include methods of treating a disease in a patient comprising administering to a patient in need thereof a therapeutically effective amount of a compound or pharmaceutical composition provided by the present disclosure, wherein the disease is selected from sudden idiopathic hearing loss, drug induced hearing loss, age-related hearing loss, and Duchenne muscular dystrophy.

Methods provided by the present disclosure include methods of treating a viral disease in a patient comprising administering to a patient in need thereof a therapeutically effective amount of a compound or pharmaceutical composition provided by the present disclosure. A viral disease can be SARS-CoV-19 and SARS-CoV-2.

The amount of a compound of Formula (1) provided by the present disclosure, or pharmaceutical composition thereof that will be effective in the treatment of a disease can depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of a compound of Formula (1) provided by the present disclosure administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of a compound of Formula (1) provided by the present disclosure and appropriate dosing intervals may be selected to maintain a sustained therapeutically effective concentration of a compound of Formula (1) provided by the present disclosure in the blood of a patient, and in certain embodiments, without exceeding a minimum adverse concentration.

A pharmaceutical composition comprising a compound of Formula (1) provided by the present disclosure may be administered, for example once per week, every 2 weeks, every 3 weeks, every 4 weeks, every 5 weeks, or every 6 weeks. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of a compound of Formula (1) provided by the present disclosure contained within each of the multiple dosage forms may be the same or different.

Suitable daily dosage ranges for administration can range, for example, from about 2 µg to about 200 mg of a compound of Formula (1) provided by the present disclosure per kilogram body weight.

Suitable daily dosage ranges for administration may range, for example, from about 1 µg to about 50 mg of a compound of Formula (1) provided by the present disclosure per square meter ($m^2$) of body surface.

A compound of Formula (1) provided by the present disclosure may be administered to treat cancer in a patient in an amount, for example, from 0.001 mg/day to 100 mg/day, or in any other appropriate daily dose. A dose can be, for example, from 0.01 µg/kg body weight/week to 100 µg/kg body weight/week or any other suitable dose.

A pharmaceutical composition comprising a compound of Formula (1) provided by the present disclosure may be administered to treat cancer in a patient so as to provide a therapeutically effective concentration of a compound of Formula (1) provided by the present disclosure in the blood or plasma of the patient. A therapeutically effective concentration of a compound of a compound of Formula (1) provided by the present disclosure in the blood of a patient can be, for example, from 0.01 g/L to 1,000 g/L, from 0.1 g/L to 500 g/L, from 1 g/L to 250 g/L, or from about 10 g/L to about 100 g/L. A therapeutically effective concentration of a compound of Formula (1) provided by the present disclosure in the blood of a patient can be, for example, at least 0.01 g/L, at least 0.1 g/L, at least 1 g/L, at least about 10 g/L, or at least 100 g/L. A therapeutically effective concentration of a compound of Formula (1) in the blood of a patient can be, for example, less than an amount that causes unacceptable adverse effects including adverse effects to homeostasis. A therapeutically effective concentration of a compound of Formula (1) in the blood of a patient can be an amount sufficient to restore and/or maintain homeostasis in the patient.

Pharmaceutical compositions provided by the present disclosure may be administered to treat a disease in a patient so as to provide a therapeutically effective concentration of a compound of Formula (1) in the blood of a patient for a period of time such as, for example, for 4 hours, 8 hours, 12 hours, 16 hours, 20 hours, 1 day, or 2 days.

The amount of a compound of Formula (1) administered may vary during a treatment regimen.

Pharmaceutical compositions provided by the present disclosure may further comprise one or more pharmaceutically active compounds in addition to a compound of Formula (1). Such compounds may be provided, for example, to treat the cancer being treated with the compound of Formula (1) or to treat a disease, disorder, or condition other than the cancer being treated with the compound of Formula (1), to treat a side-effect caused by administering the compound of Formula (1), to augment the efficacy of the compound of Formula (1), and/or to modulate the activity of the compound of Formula (1).

A compound of Formula (1) provided by the present disclosure may be administered in combination with at least one other therapeutic agent. A compound of Formula (1) may be administered to a patient together with another compound for treating cancer in the patient. The at least one other therapeutic agent can be a second, different compound of Formula (1). A compound of Formula (1) and the at least one other therapeutic agent may act additively or, and in certain embodiments, synergistically with another compound of Formula (1). The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating cancer or a different disease, disorder or condition than cancer. Methods provided by the present disclosure include administration of a compound of Formula (1) and one or more other therapeutic agents provided that the combined administration does not inhibit the therapeutic efficacy of the compound of Formula (1) and/or does not produce adverse combination effects.

A pharmaceutical composition comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain combination therapies, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising a compound of Formula (1) provided by the present disclosure may be administered with one or more substances, for example, to enhance, modulate and/or control release, bioavailability, therapeutic efficacy, therapeutic potency, and/or stability, of the compound of Formula (1). For example, a pharmaceutical composition comprising a compound of Formula (1) can be co-administered with an active agent having pharmacological effects that enhance the therapeutic efficacy of the compound of Formula (1).

A compound of Formula (1), or a pharmaceutical composition thereof may be administered in conjunction with an agent known or believed to be effective in treating a disease such as cancer, an autoimmune disease or an inflammatory disease in a patient, such as the same disease being treated with the compound of Formula (1).

A compound of Formula (1), or a pharmaceutical composition thereof may be administered in conjunction with an agent known or believed to interfere with cell proliferation.

A compound of Formula (1), or a pharmaceutical composition thereof may be administered in conjunction with an agent known or believed to interfere with cellular metabolism, to be an anti-metabolite, to interfere with RNA transcription, to interfere with RNA translation, to interfere with cellular protein synthesis, to interfere with synthesis of precursors for DNA synthesis and replication, to interfere with purine synthesis, to interfere with nucleoside synthesis, to interact with mTOR, to be an mTOR inhibitor, to interfere with cell cycle checkpoints.

A compound of Formula (1) or a pharmaceutical composition thereof may be administered in conjunction with a checkpoint inhibitor including a CTLA-4 inhibitor such as ipilimumab, a PD-1 inhibitor such as pembrolizumab and nivolumab, and/or a PD-LI inhibitor such as atezolizumab, avelumab, and durvalumab. A compound of Formula (1) or a pharmaceutical composition thereof may be administered in conjunction with an immunomodulator such as CD137/ 4-1BB, CD27, GIYR, and/or OC40.

A compound of Formula (1) or a pharmaceutical composition thereof may be administered in conjunction with an agent known or believed to be cytotoxic, to cause DNA damage, to cause cell cycle arrest, or to cause mitotic catastrophe.

A compound of Formula (1) or a pharmaceutical composition thereof may be administered in conjunction with an agent known or believed to modulate glutathione concentration, to modulate glutathione concentration within cells, to decrease glutathione concentration within cells, to reduce glutathione uptake into cells, to reduce glutathione synthesis, or to reduce glutathione synthesis within cells.

A compound of Formula (1) or a pharmaceutical composition thereof may be administered in conjunction with an agent known or believed to interfere with neovascularization, to reduce neovascularization, or to promote neovascularization.

A compound of Formula (1) or a pharmaceutical composition thereof may be administered in conjunction with an agent known or believed to interfere with hormone homeostasis, to interfere with hormone synthesis, to interfere with hormone receptor binding, or to interfere with hormone signal transduction.

A compound of Formula (1) or a pharmaceutical composition thereof may be administered in conjunction with an agent known or believed to interfere with growth factor homeostasis, to interfere with growth factor receptor expression, to interfere with growth factor binding to growth factor receptors, to interfere with growth factor receptor signal transduction, to interfere with the Hedgehog (Hh) signaling, to inhibit the Hedgehog pathway signaling, to inhibit ALK (anaplastic lymphoma kinase) pathway signaling, or to inhibit the non-homologous end joining (NHEJ) pathway.

A compound of Formula (1) or a pharmaceutical composition thereof may be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhancer of zeste homolog 2) inhibitor, a BET (bromodomain and extraterminal domain motif) inhibitor, a SYK (spleen tyrosine kinase) inhibitor, JAK (janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selective RXR activating agent, a p-glycoprotein inhibitor, a ERK inhibitor, a PI3K (phosphatidylinositol-4,5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of Moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (casein kinase) inhibitor, a CK2 inhibitor, a Bcr-Abl (breakpoint cluster region—Abelson proto-oncogene) tyrosine-kinase inhibitor such as dasatinib, a microtubule stabilizing agent, a microtubule depolymerization/disassembly inhibitor, a DNA intercalator, an androgen receptor antagonist, a chemoprotective agents, a HDAC (histone deacetylase) inhibitor, a DPP (dipeptidyl peptidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-α) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy) sensitizer, an ATR (ataxia telangiectasia- and Rad3-related protein kinase) inhibitor, or a combination of any of the foregoing.

A compound of Formula (1) or a pharmaceutical composition thereof may be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; nuclear translocations factors such as JSH-23; a PORCn inhibitor such as Wnt-C59; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTX015; a MEK5/ERK5 inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actotiamide HCl; an Erk inhibitor such SCH772984; a PI3K inhibitor such as gedatolisib; a JAK inhibitor such as ruxolitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinib HCl; an IDO inhibitor such as INCB024360; a DNA crosslinker such as mitomycin C; a tyrosine kinase inhibitor such as nilotinib, a PARP inhibitor such as olaparib; a tubulin stabilization promoter such as paclitaxel; a CDK4/6 inhibitor such as palbociclib; a RTK inhibitor such as sunitinib; a PDT sensitizer such as tslsporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

A compound of Formula (1) or a pharmaceutical composition thereof may be administered in conjunction with another chemotherapeutic agent, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, reylimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing.

A compound of Formula (1) or a pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxorubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

A compound of Formula (1) or a pharmaceutical composition thereof may be co-administered with a compound that inhibits DNA repair such as, for example, O6-benzylguanine (O6-BG).

A compound of Formula (1) or a pharmaceutical composition thereof may be administered in conjunction with one or more chemotherapeutic agents, such as, for example, abarelix, abiraterone, abiraterone acetate, n-acetyl cysteine, aclarubicin hydrochloride, adriamycin, adenine, afatinib, afatinib dimaleate, alemtuzumab, alendronate sodium, alitretinoin, allopurinol sodium, altretamine, amifostine, aminoglutethimide, aminolevulinic acid, amrubicin, amsacrine, anastrozole, angiostatin, apremilast, aprepitant, arsenic trioxide, ascorbic acid, 1-asparaginase, azacitidine, azathioprine sodium, bazedoxifene (serm), belinostat, bendamustine hcl, O6-benzylguanine, bevacizumab, bexarotene, bicalutamide, biricodar, bleomycin sulfate, bortezomib, bosutinib, brivudine, buserelin, busulfan, buthionine sulfoxime, cabazitaxel, cabozantinib, capecitabine, carboplatin, carboquone, carfilzomib, carmofur, carmustine, ceritinib, chlorambucil, cisplatin, cladribine, clodronate disodium, clofarabine, crizotinib, cyclophosphamide, cyclosporine, cytarabine, cytosine arabinoside, dabrafenib, dacarbazine, dactinomycin, dasatinib, datinomycin, daunorubicin, decitabine, defribrotide, degarelix acetate, dexamethasone, dexrazoxane hydrochloride, diaziquone, diethyl stilbestrol, docetaxel, doxifluridine, doxorubicin hydrochloride, doxorubicin free base, dromostanolone propionate, dutasteride, eltrombopag, enzalutamide, epirubicin hydrochloride, eribulin mesylate, erlotinib hydrochloride, estramustine phosphate sodium, ethinyl estradiol, etoposide phosphate, etoposide, everolimus, exemestane, fentanyl, filgrastim, fingolimod, floxuridine, fludarabine phosphate, fluorouracil, fluoxymesterone, flutamide, formestane, formylmelphalan, fosaprepitant, fotemustine, fulvestrant, gefitinib, gemcitabine hydrochloride, gemcitabine free base, glutathione, glyciphosphoramide, glyfosfin, goserelin acetate, granisetron hydrochloride, heptaplatin, hexyl 5-aminolevulinate, histrelin acetate, hydroxyprogesterone caproate, hydroxyurea, ibandronate sodium, ibrutinib, icotinib, idarubicin HCl, idelalisib, idoxuridine, ifosfamide, interferon alpha, imatinib mesylate, imiquimod, ingenol mebutate, ipilimumab, irinotecan hydrochloride, ixabepilone, lanreotide acetate, lapatinib free base, lapatinib ditosylate, lasofoxifene, lenalidomide, letrozole, leucovorin calcium, leuprolide acetate, levamisole hydrochloride, levoleucovorin calcium, iobenguane, lobaplatin, lomustine, maropitant, masoprocol, mechlorethamine hydrochloride, megestrol acetate, medroxyprogesterone acetate, melphalan hydrochloride, mercaptopurine, mercaptoethane sulfonate sodium, methotrexate, methoxsalen, methyl aminolevulinate, methylene blue, methylisoindigotin, mifamurtide, miltefosine, miriplatin, mithamycin, mitobronitol, mitomycin C, mitotane, mitoxantrone hydrochloride, mycophenolate mofetil, nabiximols, nafarelin, nandrolone, nedaplatin, nelarabine, netupitant, nilotinib, nilutamide, nimustine, nintedanib, nocodazole, octreotide, olaparib, omacetaxine mepesuccinate, ondansetron hydrochloride, oxaliplatin, paclitaxel, palbociclib, palifermin, palonosetron hydrochloride, pamidronate disodium, panobinostat, pasireotide, pazopanib hydrochloride, pegfilrastim, pemetrexed disodium, pentostatin, peplomycin, pipobroman, pirarubicin, plerixafor, plicamycin, pomalidomide, ponatinib, porfimer sodium, porfiromycin, pralatrexate, prednimustine, prednisolone, prednisone, procarbazine hydrochloride, quinagolide hydrochloride, raloxifene, raltitrexed, radotinib, ranimustine, retinoic acids, reylimid, rituxinab, romidepsin, ruxolitinib, ruxolitinib phosphate, semustine, sirolimus, sodium thiosulfate, sorafenib free base, sorafenib tosylate, streptozocin, sufentanil, sunitinib, tacrolimus, talaporfin sodium, tamibarotene, tamoxifen citrate, tapentadol, http://www.medkoo.com/Anticancer-approved/Tegafur.html temoporfin, temozolomide, temsirolimus, teniposide, teriflunomide, tertiposide, testolactone, testosterone propionate, thalidomide, thioguanine, thiotepa, thymalfasin, toceranib phosphate, topotecan hydrochloride, toremifene citrate, trabectedin, trametinib, tretinoin, trilostane, triptorelin, tropisetron, uramustine, valrubicin, vandetanib, vedotin, vemurafenib, verteporfin, vinblastine, vincristine sulfate, vincristine free base, vindesine, vinorelbine tartrate, vorinostat, and zoledronic acid.

A compound of Formula (1) or a pharmaceutical composition thereof may be administered in conjunction with one or more chemotherapeutic agents such as, for example, abemaciclib, abiraterone acetate, ABVD, ABVE, ABVE-PC, AC, acalabrutinib, AC-T, ADE, ado-trastuzumab emtansine, afatinib dimaleate, aldesleukin, alectinib, alemtuzumab, alpelisib, amifostine, aminolevulinic acid hydrochloride, anastrozole, apalutamide, aprepitant, arsenic trioxide, asparaginase Erwinia chrysanthemi, atezolizumab, avelumab, axicabtagene ciloleucel, axitinib, azacitidine, BEACOPP, belinostat, bendamustine hydrochloride, BEP, bevacizumab, bexarotene, bicalutamide, binimetinib, bleomycin sulfate, blinatumomab, bortezomib, bosutinib, brentuximab vedotin, brigatinib, BuMel, busulfan, cabazitaxel, cabozantinib-s-malate, CAF, calaspargase pegol-mknl, capecitabine, caplacizumab-yhdp, CAPOX, carboplatin, carboplatin-taxol, carfilzomib, carmustine, carmustine implant, CEM, cemiplimab-rwlc, ceritinib, cetuximab, CEV, chlorambucil, chlorambucil-prednisone, CHOP, cisplatin, cladribine, clofarabine, CMF, cobimetinib, copanlisib hydrochloride, COPDAC, COPP, COPP-ABV, crizotinib, CVP, cyclophosphamide, cytarabine, cytarabine liposome, dabrafenib mesylate, dacarbazine, dacomitinib, dactinomycin, daratumumab, darbepoetin α, dasatinib, daunorubicin hydrochloride, daunorubicin hydrochloride and cytarabine liposome, decitabine, defibrotide sodium, degarelix, denileukin diftitox, denosumab, dexamethasone, dexrazoxane hydrochloride, dinutuximab, docetaxel, doxorubicin hydrochloride, doxorubicin hydrochloride liposome, durvalumab, duvelisib, elotuzumab, eltrombopag olamine, emapalumab-lzsg, enasidenib mesylate, encorafenib, enzalutamide, epirubicin hydrochloride, EPOCH, epoetin α, erdafitinib, eribulin mesylate, erlotinib hydrochloride, etoposide, etoposide phosphate, everolimus, exemestane, fec, filgrastim, fludarabine phosphate, fluorouracil injection, fluorouracil—topical, flutamide, folfiri, folfiri-bevacizumab, folfiri-cetuximab, folfirinox, folfox, fostamatinib disodium, FU-LV, fulvestrant, gefitinib, gemcitabine hydrochloride, gemcitabine-cisplatin, gemcitabine-oxaliplatin, gemtuzumab ozogamicin, gilteritinib fumarate, glasdegib maleate, glucarpidase, goserelin acetate, granisetron, HPV bivalent vaccine, HPV bivalent vaccine, recombinant HPV nonavalent vaccine, HPV nonavalent vaccine, recombinant, HPV quadrivalent vaccine, HPV uadrivalent vaccine recombinant, hydroxyurea, hyper-CVAD, ibritumomab tiuxetan, ibrutinib, ICE, idarubicin hydrochloride, idelalisib, ifosfamide, imatinib mesylate, imiquimod, inotuzumab ozogamicin, interferon α-2b recombinant, iobenguane $^{131}$I, ipilimumab, irinotecan hydrochloride, irinotecan hydrochloride liposome, ivosidenib, ixabepilone, ixazomib citrate, JEB, lanreotide acetate, lapatinib ditosylate, larotrectinib sulfate, lenalidomide, lenvatinib mesylate, letrozole, leucovorin calcium, leuprolide acetate, lomustine, lorlatinib, lutetium Lu 177-dotatate, mechlorethamine hydrochloride, megestrol acetate, melphalan, melphalan hydrochloride, mercaptopurine, mesna, methotrexate, methylnaltrexone bromide, midostaurin, mitomycin c, mitoxantrone hydrochloride, mogamulizumab-kpkc, moxetumomab pasudotox-tdfk, MVAC, necitumumab, nelarabine, neratinib maleate, netupitant and palonosetron hydrochloride, nilotinib, nilutamide, niraparib tosylate monohydrate, nivolumab, obinutuzumab, OEPA, ofatumumab, OFF, olaparib, olaratumab, omacetaxine mepesuccinate, ondansetron hydrochloride, OPPA, osimertinib mesylate, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, pazopanib hydrochloride, PCV, PEB, pegaspargase, pegfilgrastim, peginterferon α-2b, pembrolizumab, pemetrexed disodium, pertuzumab, plerixafor, polatuzumab vedotin-piiq, pomalidomide, ponatinib hydrochloride, pralatrexate, prednisone, procarbazine hydrochloride, propranolol hydrochloride, radium 223 dichloride, raloxifene hydrochloride, ramucirumab, rasburicase, ravulizumab-cwvz, R-CHOP, R-CVP, recombinant HPV bivalent vaccine, recombinant HPV nonavalent vaccine, recombinant HPV quadrivalent vaccine, recombinant interferon α-2b, regorafenib, R-EPOCH, ribociclib, R-ICE, rituximab, rituximab and hyaluronidase human, rolapitant hydrochloride, romidepsin, romiplostim, rucaparib camsylate, ruxolitinib phosphate, siltuximab, sipuleucel-t, sonidegib, sorafenib tosylate, STANFORD V, sunitinib malate, TAC, tagraxofusp-erzs, talazoparib tosylate, talc, talimogene laherparepvec, tamoxifen citrate, temozolomide, temsirolimus, thalidomide, thioguanine, thiotepa, tisagenlecleucel, tocilizumab, topotecan hydrochloride, toremifene, TPF, trabectedin, trametinib, trastuzumab, trastuzumab and hyaluronidase-oysk, trifluridine and tipiracil hydrochloride, uridine triacetate, VAC, Valrubicin, VAMP, vandetanib, VeIP, vemurafenib, venetoclax, vinblastine sulfate, vincristine sulfate liposome, vinorelbine tartrate, vip, vismodegib, vorinostat, XELIRI, XELOX, Ziv-aflibercept, zoledronic acid, and combinations of any of the foregoing.

A compound provided by the present disclosure or a pharmaceutically acceptable salt thereof or a pharmaceutical composition thereof can be administered to a patient in conjunction with another compound known to be useful for treating the inflammatory disease, the autoimmune diseases, or the age-related disease being treated by the compound provided by the present disclosure.

The efficacy of administering a compound of Formula (1) or a pharmaceutical composition thereof for treating cancer, an inflammatory disease, or an autoimmune disease may be assessed using in vitro and animal studies and in clinical trials.

ASPECTS OF THE INVENTION

The invention is further defined by one or more of the following aspects.

Aspect 1. The compound 1,1-dioxido-2,3-dihydrothiophen-3-yl 4-phenoxybenzenesulfonate having the structure of Formula (1):

(1)

or a pharmaceutically acceptable salt thereof.

Aspect 2. The compound of aspect 1, wherein the compound is (S)-1,1-dioxido-2,3-dihydrothiophen-3-yl 4-phenoxybenzenesulfonate (1a):

(1a)

or a pharmaceutically acceptable salt thereof.

Aspect 3. The compound of aspect 1, wherein the compound is (R)-1,1-dioxido-2,3-dihydrothiophen-3-yl 4-phenoxybenzenesulfonate (1b):

(1b)

or a pharmaceutically acceptable salt thereof.

Aspect 4. The compound of any one of aspects 1 to 3, wherein the compound is the free base.

Aspect 5. The compound of any one of aspects 1 to 3, wherein the compound is the hydrochloric acid salt.

Aspect 6. A pharmaceutical composition comprising the compound of any one of aspects 1 to 5 or a pharmaceutically acceptable salt thereof.

Aspect 7. A method of treating a disease in a patient comprising administering to a patient in need of such treatment a therapeutically effective amount of the compound of any one of aspects 1 to 5 or a pharmaceutically acceptable salt thereof, wherein the disease is treated by inhibiting extracellular signal-regulated kinase 1 and/or extracellular signal-regulated kinase 2.

Aspect 8. A method of treating a disease in a patient comprising administering to a patient in need of such treatment a therapeutically effective amount of the compound of any one of aspects 1 to 5 or a pharmaceutically acceptable salt thereof, wherein the disease is selected from cancer, an inflammatory disease, an autoimmune disease, or a pulmonary disease.

Aspect 9. A method of treating a disease in a patient comprising administering to a patient in need of such treatment a therapeutically effective amount of the pharmaceutical composition of aspect 6, wherein the disease is treated by inhibiting extracellular signal-regulated kinase 1 and/or extracellular signal-regulated kinase 2.

Aspect 10. A method of treating a disease in a patient comprising administering to a patient in need of such treatment a therapeutically effective amount of the pharmaceutical composition of aspect 6, wherein the disease is selected from cancer, an inflammatory disease, an autoimmune disease, or a pulmonary disease.

EXAMPLES

The following examples describe in detail the synthesis of compounds of Formula (1), the characterization of compounds of Formula (1) and uses of compounds of Formula (1). It will be apparent to those skilled in the art that many modifications, both to materials and methods, may be practiced without departing from the scope of the disclosure.

Example 1

Synthesis of 3-hydroxy-2,3-dihydrothiophene 1,1-dioxide

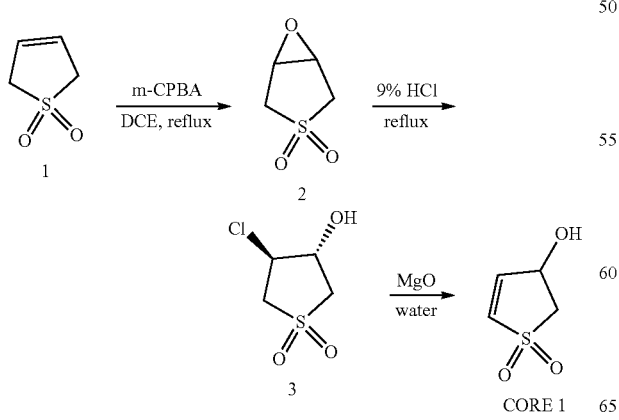

Step 1: Synthesis of 6-Oxa-2-thiabicyclo[3.1.0]hexane 3,3,-dioxide (2)

To a solution of 2,5-dihydrothiophene 1,1-dioxide (1) (100.0 g, 0.85 mol) in 1,2-dichloroethane (DCE) (1600 mL) was added metal-chloroperoxybenzoic acid (m-CPBA) (365.1 g, 2.12 mol) at 0° C. The reaction mixture was stirred at 80° C. for 2 days. The reaction mixture was cooled to 0° C., quenched with sat. $Na_2SO_3$ (aq) (1 L), stirred at room temperature for 30 min and filtered. The filtrate was extracted with dichloromethane (DCM) (400 mL×2), the combined organic layers washed with water, and brine, and concentrated in vacuum. The concentrate was purified busing silica gel column (petroleum ether/EtOAc=10/1 to 1/1, v/v) and washed by $Et_2O$ to afford compound (2) (70.0 g, 61.65% yield) as a white solid. $^1$H NMR (400 MHz, DMSO-$d_6$) δ 3.99 (dd, J=2.1, 0.9 Hz, 2H), 3.68-3.52 (m, 2H), 3.39 (d, J=14.7 Hz, 2H).

Step 2: Synthesis of (3S,4R)-3-Chloro-4-hydroxytetrahydrothiophene 1,1-dioxide (3)

Compound (2) (70 g, 521.8 mmol) was dissolved in 9% HCl aq (1200 mL) and the mixture was heated to reflux 16 h. The mixture was cooled to 0° C. and filtered. The filter cake was washed with water and dried to afford compound (3) (50 g, 56.16% yield) as a white solid. $^1$H NMR (400 MHz, DMSO-$d_6$) δ 6.31 (d, J=4.2 Hz, 1H), 4.57-4.59 (m, 1H), 4.56-4.46 (m, 1H), 3.77 (dd, J=14.2, 6.3 Hz, 1H), 3.55 (dd, J=13.8, 5.8 Hz, 1H), 3.43 (dd, J=14.2, 4.1 Hz, 1H), 3.12 (dd, J=13.8, 3.6 Hz, 1H).

Step 3: Synthesis of 3-hydroxy-2,3-dihydrothiophene 1,1-dioxide (CORE 1)

To a solution of (3S,4R)-3-chloro-4-hydroxytetrahydrothiophene 1,1-dioxide (3) (50 g, 293.1 mmol) in water (500 mL) was added MgO (5.91 g, 146.5 mmol). The mixture was stirred at room temperature for 16 h. The mixture was filtered and concentrated, purified by silica column (petroleum ether:EtOAc=5/1 to 1:1) to afford CORE 1 (20 g, 50.87% yield) as colorless oil. $^1$H NMR (400 MHz, DMSO-d6) δ 7.07 (dd, J=6.7, 1.5 Hz, 1H), 6.82 (dd, J=6.7, 2.7 Hz, 1H), 6.04 (d, J=6.2 Hz, 1H), 5.14-4.78 (m, 1H), 3.67 (dd, J=13.8, 7.4 Hz, 1H), 2.93 (dd, J=13.8, 3.8 Hz, 1H).

Example 2

Synthesis of 1,1-dioxido-2,3-dihydrothiophen-3-yl 4-phenoxybenzenesulfonate (1)

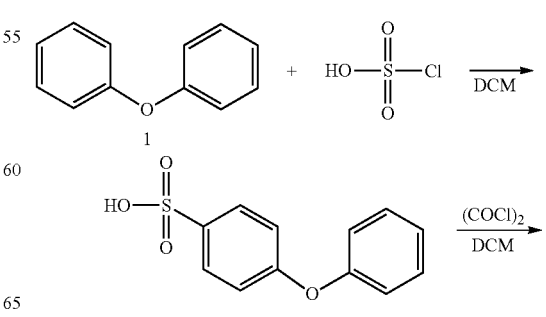

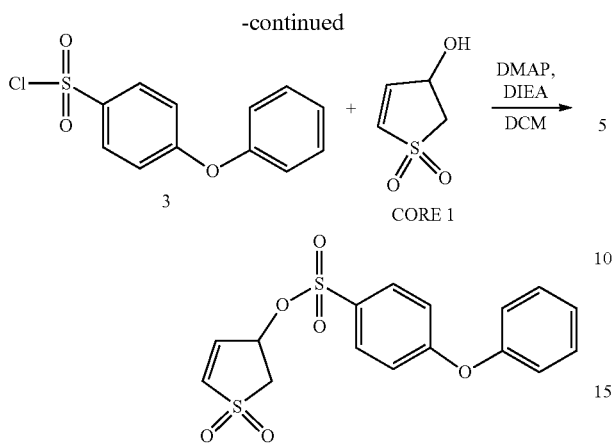

Step 1: Synthesis of 4-phenoxybenzenesulfonic Acid

To a solution of oxydibenzene (2.0 g, 11.75 mmol) in DCM (60 mL) was added sulfurochloridic acid (1.37 g, 11.75 mol) at 0° C. The mixture was stirred at 23° C. for 2 h. The mixture was concentrated in vacuum to afford crude 4-phenoxybenzenesulfonic acid (2.8 g, 95.2%) as yellow oil. $^1$H NMR: (400 MHz, chloroform-d) δ 9.89 (s, 1H), 7.75 (d, J=8.4 Hz, 2H), 7.36 (t, J=7.8 Hz, 2H), 7.17 (t, J=7.5 Hz, 1H), 7.03-6.99 (m, 2H), 6.92 (d, J=8.4 Hz, 2H).

Step 2. Synthesis of 4-phenoxybenzenesulfonyl Chloride

To a solution of 4-phenoxybenzenesulfonic acid (500.0 mg, 2.0 mmol) in DCM (5 mL) was added (COCl)$_2$ (304.3 mL, 2.4 mmol) at 0° C. The mixture was stirred at 23° C. for 2 h. The reaction mixture was diluted with water (20 mL) and extracted with DCM (10 mL×2). The combined organic phase was washed by water (20 mL) and brine (20 mL), dried over Na$_2$SO$_4$, concentrated in vacuum, and purified by silica gel column (petroleum ether/EtOAc=200/1 to 50/1, v/v) to afford 4-phenoxybenzenesulfonyl chloride (351 mg, 65.2%) as colorless oil. $^1$H NMR: (400 MHz, chloroform-d) δ 8.01-7.95 (m, 2H), 7.49-7.42 (m, 2H), 7.31-7.26 (m, 1H), 7.14-7.04 (m, 4H).

Step 3. Synthesis of 1,1-dioxido-2,3-dihydrothiophen-3-yl 4-phenoxybenzenesulfonate (1)

To a solution of 3-hydroxy-2,3-dihydrothiophene 1,1-dioxide (50 mg, 0.37 mmol) in DCM (2 mL) was added DMAP (2.2 mg, 0.018 mmol), DIEA (58.1 mg, 0.45 mmol) and 4-phenoxybenzenesulfonyl chloride (116.8 mg, 0.41 mmol) at 0° C. The reaction mixture was stirred at 23° C. for 2 h. The mixture was diluted with water (20 mL), extracted with DCM (10 mL×2). The combined organic phase was washed by water (20 mL) and brine (20 mL), dried over Na$_2$SO$_4$, and concentrated in vacuum and purified by silica gel column (petroleum ether/EtOAc=5/1, v/v) and Prep-TLC (Pet. ether/EtOAc=2/1, v/v) to afford 1,1-dioxido-2,3-dihydrothiophen-3-yl 4-phenoxybenzenesulfonate (15.0 mg, 23.3% yield) as a white solid. $^1$H NMR (400 MHz, chloroform-d) δ 7.86 (d, J=8.9 Hz, 2H), 7.45 (t, J=7.1 Hz, 2H), 7.29 (d, J=6.7 Hz, 1H), 7.10 (dd, J=8.6, 3.3 Hz, 4H), 6.84 (d, J=6.7 Hz, 1H), 6.69 (dd, J=6.7, 2.6 Hz, 1H), 5.74-5.67 (m, 1H), 3.59 (dd, J=14.2, 7.6 Hz, 1H), 3.29 (dd, J=14.2, 3.9 Hz, 1H). LCMS: Time=2.075 min, C$_{16}$H$_{14}$O$_6$S$_2$; [M+18]=384.1, [M+23]=389.0.

Example 3

Synthesis of (S)-1,1-Dioxido-2,3-dihydrothiophen-3-yl 4-phenoxybenzenesulfonate (1a)

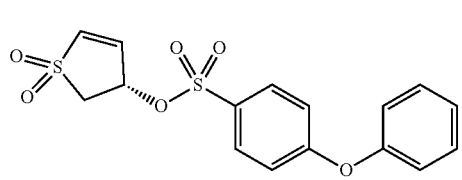

1,1-Dioxido-2,3-dihydrothiophen-3-yl 4-phenoxybenzenesulfonate (1) prepared as described in Example 2 (500.0 mg, 1.86 mmol) was purified by chiral separation to afford (S)-1,1-dioxido-2,3-dihydrothiophen-3-yl 4-phenoxybenzenesulfonate (1a) (100.4 mg, 20% yield) as white solid. Chiral separation method: Column: Chiralcel®OJ-H, column size: 4.6 mm I.D×25 cm, 5 m, Injection: 5 μL, mobile phase: 100% EtOH, Flow rate: 1.0 ml/min, wavelength: UV 254 nm, temperature: 35° C., Sample solution: 1.0 mg/mL in MeOH (50%) and EtOH (50%), HPLC equipment: Shimadzu 2020. $^1$H NMR (400 MHz, CDCl$_3$) δ 7.86 (d, J=8.8 Hz, 2H), 7.45 (t, J=7.9 Hz, 2H), 7.29 (t, J=7.4 Hz, 1H), 7.14-7.06 (m, 4H), 6.85 (dd, J=6.8, 1.5 Hz, 1H), 6.69 (dd, J=6.7, 2.8 Hz, 1H), 5.73-5.69 (m, 1H), 3.59 (dd, J=14.2, 7.6 Hz, 1H), 3.29 (dd, J=14.2, 3.9 Hz, 1H). LCMS: SJJ-2943-053, 2.071 m/z: 384.1[M+18]$^+$. HPLC: 11.610 min, m/z, 98.76% at 254 mm, 98.68% at 214 mm. ee=95.28%.

Example 4

Synthesis of (R)-1,1-Dioxido-2,3-dihydrothiophen-3-yl 4-phenoxybenzenesulfonate (1b)

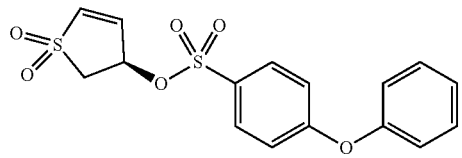

1,1-Dioxido-2,3-dihydrothiophen-3-yl 4-phenoxybenzenesulfonate (1) prepared as described in Example 2 (500.0 mg, 1.86 mmol) was purified by chiral separation to afford (R)-1,1-dioxido-2,3-dihydrothiophen-3-yl 4-phenoxybenzenesulfonate (1b) (100.5 mg, 20% yield) as white solid. Chiral separation method: Column: Chiralcel®OJ-H, column size: 4.6 mm ID×25 cm, 5 μm, Injection: 5 μL, mobile phase: 100% EtOH, Flow rate: 1.0 mL/min, wavelength: UV 254 nm, temperature: 35° C., Sample solution: 1.0 mg/mL in MeOH (50%) and EtOH (50%), HPLC equipment: Shimadzu 2020. $^1$H NMR (400 MHz, CDCl$_3$) δ 7.86 (d, J=9.0 Hz, 2H), 7.45 (t, J=7.9 Hz, 2H), 7.29 (t, J=7.4 Hz, 1H), 7.14-7.06 (m, 4H), 6.85 (dd, J=6.7, 1.6 Hz, 1H), 6.69 (dd, J=6.8, 2.8 Hz, 1H), 5.76-5.66 (m, 1H), 3.59 (dd, J=14.2, 7.7 Hz, 1H), 3.29 (dd, J=14.2, 3.9 Hz, 1H). LCMS: SJJ-2943-

053, 2.040 m/z: 384.1[M+18]+. HPLC: 11.595 min, m/z, 99.07% at 254 mm, 98.78% at 214 mm. ee=95.45%.

Example 5

Cytotoxicity in Cancer Cell Lines

The cytotoxicity of test compounds was determined for several cell lines including melanoma cell line RPMI-7951, melanoma cell line Sk-Mel-28, melanoma cell line A375, melanoma cell line U87, glioblastoma cell line U87, immortalized human T lymphocyte Jurkat cells, and human pancreatic carcinoma cell line PL45.

All cells were obtained from ATCC. RPMI, DMEM, EMEM and pen/strep were obtained from Invitrogen. Normocin® was obtained from InvivoGen. FBS was obtained from Gibco. Cell viability reagent Cell-titer glow was obtained from Promega. All test compounds were synthesized as described herein.

The growth media for RPMI and Sk-mel-28 cells was EMEM supplemented with antibiotic/anti-mycotic pen/strep and Normocin® (InvivoGen) and 10% FBS.

The growth media for A375 and PL45 cells was DMEM supplemented with antibiotic/anti-mycotic pen/strep and Normocin® (InvivoGen) and 10% FBS.

The growth media for Jurkat cells and PBMCs was RPMI supplemented with antibiotic/anti-mycotic pen/strep and Normocin® (InvivoGen) and 10% FBS (fetal bovine serum).

Ten (10) mM solutions of each of the test compounds were prepared in dimethyl sulfoxide (DMSO) and serially diluted in DMSO to provide solutions having concentrations of the test compound of 3 mM, 1 mM, 0.3 mM, 0.1 mM, 0.03 mM, or 0.01 mM. Forty (40) μL of each of the solutions were further diluted to 400 μL in the cell specific complete media to provide 10× stock solutions having a 1 mM, 300 μM, 100 μM, 30 μM, 10 μM, 3 μM, 1 μM, or 0.3 μM of the test compound. Ten (10) μL of DMSO was diluted to 400 μL in the complete media and used as the 0 μM control.

For the cytotoxicity studies, all cells were grown in their respective complete media. Confluent cells were harvested and plated into two 96-well tissue culture treated plates at 5,000-8,000 cells/wells in 180 μL media. Twenty (20) μL of each of the 10× stock solutions were added to the wells and mixed.

After 24 hours of culture, media was aspirated out and replaced with 180 μL/well of the fresh media and 20 μL/well of the 10× stock solutions in duplicate wells in duplicate plates (Plates 1 and 2; and 3 and 4) and in quadruplicate wells (Plate 5) were added, mixed and cultured for 48 hours. The final concentrations of each test compound were 100 μM, 30 μM, 10 μM, 3 μM, 1 μM, 0.3 μM, 0.1 μM and 0 μM.

After 48 hours and/or 72 hours following addition of the test compounds, one plate each was removed from the incubator, the media aspirated out, 100 μL of CellTiter-Glo® reagent added to each well, and the resulting luminescent signals measured using a VICTOR-2® plate reader.

The data from the plate reader were exported to GraphPad (Prism) and data processed using non-linear regression and EC-50 value determined.

The cytotoxicity EC50 values (mean of three tests) for each of the test compounds with respect to the various cell lines is presented in Table 1 (48 hours) and Table 2 (72 hours).

TABLE 1

Cytotoxicity EC50 at 48 hours.

| Compound | Cell lines | | | | | |
|---|---|---|---|---|---|---|
| | RPMI | A375 | Sk mel | U87 | Jurkat | PL45 |
| 1 | 0.6 | 2.5 | 2.1 | 1.3 | 0.4 | 2.1 |
| 1a | [1] — | 1.3 | — | — | — | 2.1 |
| 1b | — | 2.5 | — | — | — | 3.0 |

[1] Not measured.

TABLE 2

Cytotoxicity EC50 at 72 hours.

| Compound | Cell lines | | | | | |
|---|---|---|---|---|---|---|
| | RPMI | A375 | Sk mel | U87 | Jurkat | PL45 |
| 1 | 0.2 | 13 | 3.1 | 0.9 | 0.2 | 0.2 |

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. The compound 1,1-dioxido-2,3-dihydrothiophen-3-yl 4-phenoxybenzenesulfonate having the structure of Formula (1):

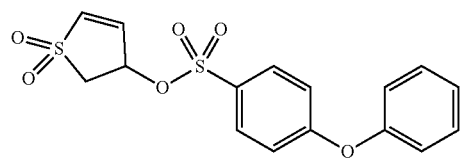

(1)

or a pharmaceutically acceptable salt thereof.

2. The compound of claim 1, wherein the compound is (S)-1,1-dioxido-2,3-dihydrothiophen-3-yl 4-phenoxybenzenesulfonate (1a):

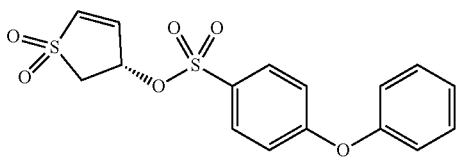

(1a)

or a pharmaceutically acceptable salt thereof.

3. The compound of claim 1, wherein the compound is (R)-1,1-dioxido-2,3-dihydrothiophen-3-yl 4-phenoxybenzenesulfonate (1b):

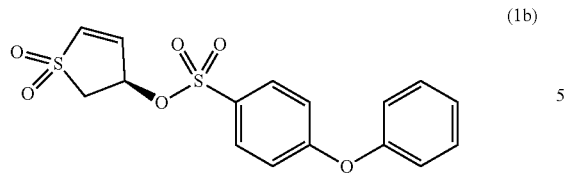
(1b)

or a pharmaceutically acceptable salt thereof.

4. The compound of claim 1, wherein the compound is the free base.

5. The compound of claim 1, wherein the compound is the hydrochloric acid salt.

6. A pharmaceutical composition comprising the compound of claim 1 or a pharmaceutically acceptable salt thereof.

7. The compound of claim 2, wherein the compound is the free base.

8. The compound of claim 2, wherein the compound is the hydrochloric acid salt.

9. A pharmaceutical composition comprising the compound of claim 2 or a pharmaceutically acceptable salt thereof.

10. The compound of claim 3, wherein the compound is the free base.

11. The compound of claim 3, wherein the compound is the hydrochloric acid salt.

12. A pharmaceutical composition comprising the compound of claim 3 or a pharmaceutically acceptable salt thereof.

* * * * *